(12) United States Patent
Drake et al.

(10) Patent No.: US 8,147,275 B1
(45) Date of Patent: Apr. 3, 2012

(54) INTERFACE ADAPTERS FOR IMPLANTABLE MEDICAL ELECTRICAL LEADS HAVING A SIDEWALL WITH AN OPENING WITH A CANTED EDGE

(75) Inventors: Ronald A. Drake, St. Louis Park, MN (US); Stanten C. Spear, Arden Hills, MN (US); Lester O. Stener, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/015,154

(22) Filed: Jan. 27, 2011

(51) Int. Cl.
*H01R 25/00* (2006.01)
*H01R 24/04* (2006.01)
*A61N 1/02* (2006.01)

(52) U.S. Cl. ......................... 439/638; 439/668; 607/115

(58) Field of Classification Search .................. 439/638, 439/668, 669, 359; 607/115–123
See application file for complete search history.

(56) References Cited

U.S. PATENT DOCUMENTS

| 5,354,326 | A | 10/1994 | Comben |
| 5,931,861 | A * | 8/1999 | Werner et al. .................. 607/115 |
| 6,343,233 | B1 * | 1/2002 | Werner et al. .................. 607/119 |
| 6,921,295 | B2 * | 7/2005 | Sommer et al. ............... 439/668 |
| 7,130,699 | B2 | 10/2006 | Huff et al. |
| 7,753,696 | B2 | 7/2010 | Hoecke et al. |

* cited by examiner

*Primary Examiner* — Chandrika Prasad
(74) *Attorney, Agent, or Firm* — Reed A. Duthler

(57) ABSTRACT

An interface adapter for an implantable medical electrical lead facilitates temporary electrical connection between an external medical device and a connector terminal of the lead. A sidewall of the adapter surrounds a receptacle of the adapter and includes a contact opening formed therethrough, to the receptacle; the sidewall further includes at least one external feature that holds a connector member of the external medical device in a tilted orientation. The tilted orientation biases a contact surface of the connector member through the contact opening and into electrical contact with an exposed connector contact of the lead connector terminal, when the terminal is inserted within the receptacle of the adapter.

33 Claims, 6 Drawing Sheets

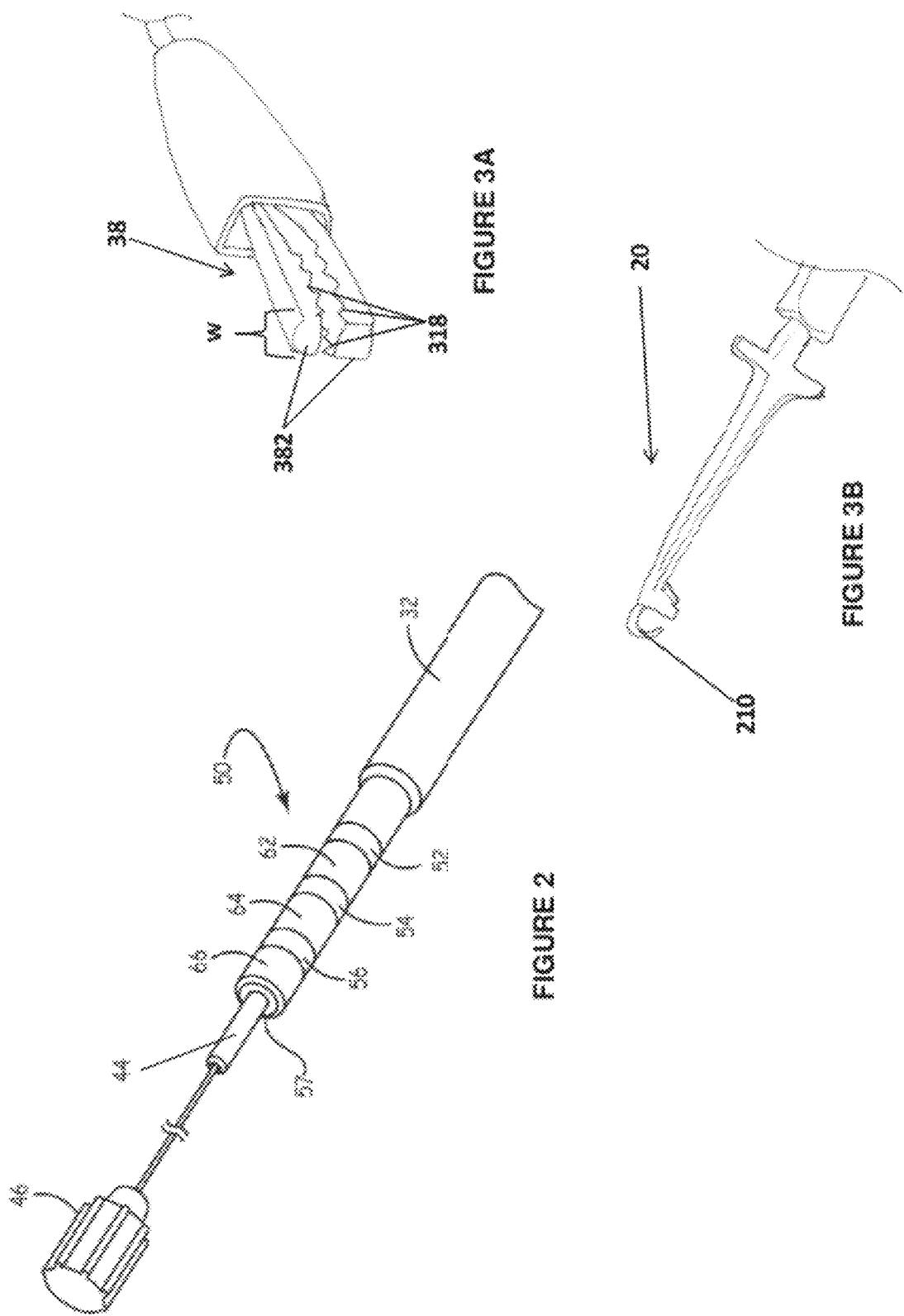

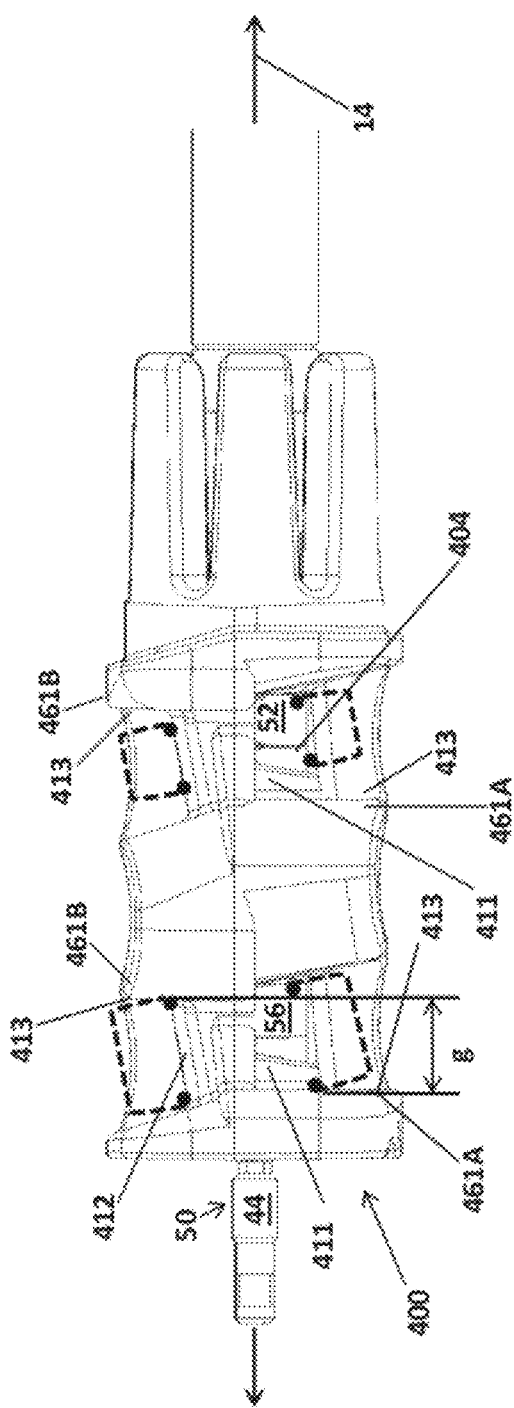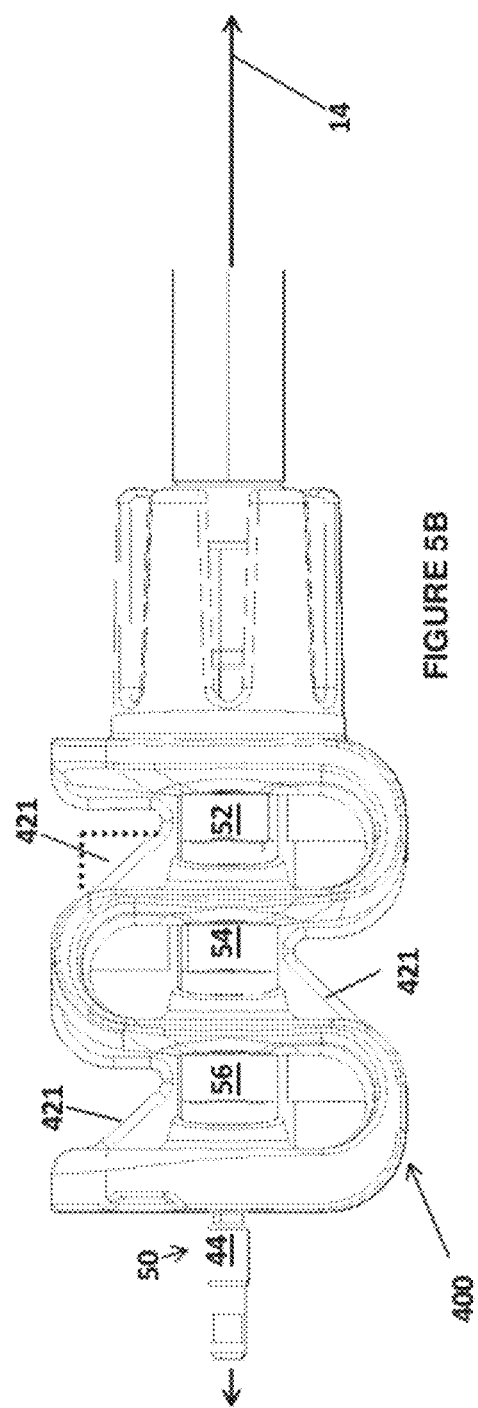

INTERFACE ADAPTERS FOR IMPLANTABLE MEDICAL ELECTRICAL LEADS HAVING A SIDEWALL WITH AN OPENING WITH A CANTED EDGE

TECHNICAL FIELD

The present invention pertains to adapters for implantable medical electrical leads and more particularly to adapters that provide an interface facilitating temporary electrical connection with a medical device.

BACKGROUND

Prior to permanently coupling an implanted medical electrical lead to the corresponding implantable pulse generator, an evaluation of sensing and/or stimulation efficacy is typically conducted to assure that electrodes and/or other types of sensors and/or therapy delivery members of the implanted lead are properly positioned. External medical devices, for example, pace sense analyzers (PSA) or neurological screeners, depending upon the type of lead and therapy delivery, are typically employed to carry out these implant evaluations. These medical devices include electrical connection cables that have contact members for making a temporary electrical connection with connector contacts of the implanted lead. The lead connector contacts are typically formed on a proximal connector terminal of the implantable medical electrical lead, which connector terminal extends out from the patient's body prior to coupling with the implantable pulse generator. Many lead connector terminals are formed with connector contact surfaces that are of sufficient size and spacing to accommodate relatively simple and reliable temporary connection with typical contact members, such as the alligator-type clip and the j-type clip known in the art, which are employed by the aforementioned connection cables. However, in the interest of increasing lead functionality by multiplying the number of therapy delivery members (i.e. electrodes) carried by the lead without unduly increasing the size/bulk of the lead, some connector terminals are of a more compact design/form (i.e. reduced connector contact surface area), which can compromise the relative ease and reliability of making these temporary electrical connections. One such connector terminal design/form is dictated by a relatively new international standard, ISO/FDIS 27186:2009(E), commonly known as the IS-4 standard, for four-pole connector terminals of cardiac pacing and defibrillation leads. Various adapters designed to couple with IS-4 connector terminals, and the like, in order to provide an enhanced interface that facilitates temporary electrical connection with external medical devices for lead implant evaluation, are known in the art, for example, as described in commonly-assigned U.S. Pat. No. 7,130,699. However, there is still a need for new adapters that are designed to provide a more robust interface for these temporary connections, without compromising ease of use and lead integrity.

SUMMARY

A sidewall of an interface adapter for an implantable medical electrical lead includes a sidewall, which surrounds a receptacle sized to receive insertion of a connector terminal of the lead therein, a contact opening, which is formed through the sidewall, and at least one external feature that holds a connector member of an electrical connection cable of an external medical device in a tilted orientation; wherein the tilted orientation biases a contact surface of the connector member through the contact opening and into electrical contact with an exposed connector contact of the lead connector terminal, when the terminal is inserted within a receptacle of the adapter. According to some embodiments, the contact opening is adjacent to a canted external edge of the sidewall which has a surface area that extends at an angle with respect to a longitudinal axis of the interface adapter and provides an interface to hold the contact member in the tilted orientation, at substantially the same angle. Alternately, or in addition, according to some embodiments, the sidewall includes a ridge protruding outward from the contact opening, wherein the ridge includes a first laterally extending portion and a second laterally extending portion, and facing surfaces of the first and second portions extend approximately perpendicular to the longitudinal axis, on opposite sides of the axis, to create a gap between which opposing jaws of the contact member, of a given width, fit in the tilted orientation. The contact opening may be one of a plurality of similar contact openings spaced apart from one another along a length of the adapter to expose a plurality of connector contacts of the inserted lead connector terminal for temporary.

According to some preferred embodiments, the canted external edge is one of a pair of canted external edges, wherein a surface area of a first of the pair extends from a laterally extending side of the contact opening in one of a proximal direction and a distal direction along the longitudinal axis of the interface adapter, while a second of the pair is located on an opposite side of the longitudinal axis of the interface adapter, from the first canted external edge, and has a surface area that extends in the other of the proximal and distal directions along the longitudinal axis. Both surface areas of the pair of canted external edges may provide an interface for an alligator-type clip contact, to bias a contact surface thereof through the contact opening, and, according to yet further embodiments, a third external edge extends from a longitudinally extending side of the contact opening to, alternately, align another type of contact member of the electrical connection cable, for example, a j-type clip, with the contact opening.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings wherein like numerals denote like elements.

FIG. 2 is a perspective view of an exemplary connector terminal of an implantable medical electrical lead.

FIGS. 3A-B are perspective views of two types of exemplary contact members that are commonly employed by external medical devices for temporary electrical connection with connector terminals of implanted medical electrical leads.

FIGS. 5A-B are side and top views of the interface adapter assembled onto the connector terminal, according to some embodiments.

DETAILED DESCRIPTION

The following detailed description is exemplary in nature and is not intended to limit the scope, applicability, or configuration of the invention in any way. Rather, the following description provides practical illustrations for implementing exemplary embodiments of the present invention. Examples of constructions, materials, dimensions and manufacturing processes are provided for selected elements, and all other elements employ that which is known to those skilled in the field of the invention. Those skilled in the art will recognize that some of the examples may have suitable alternatives.

Figure 1:
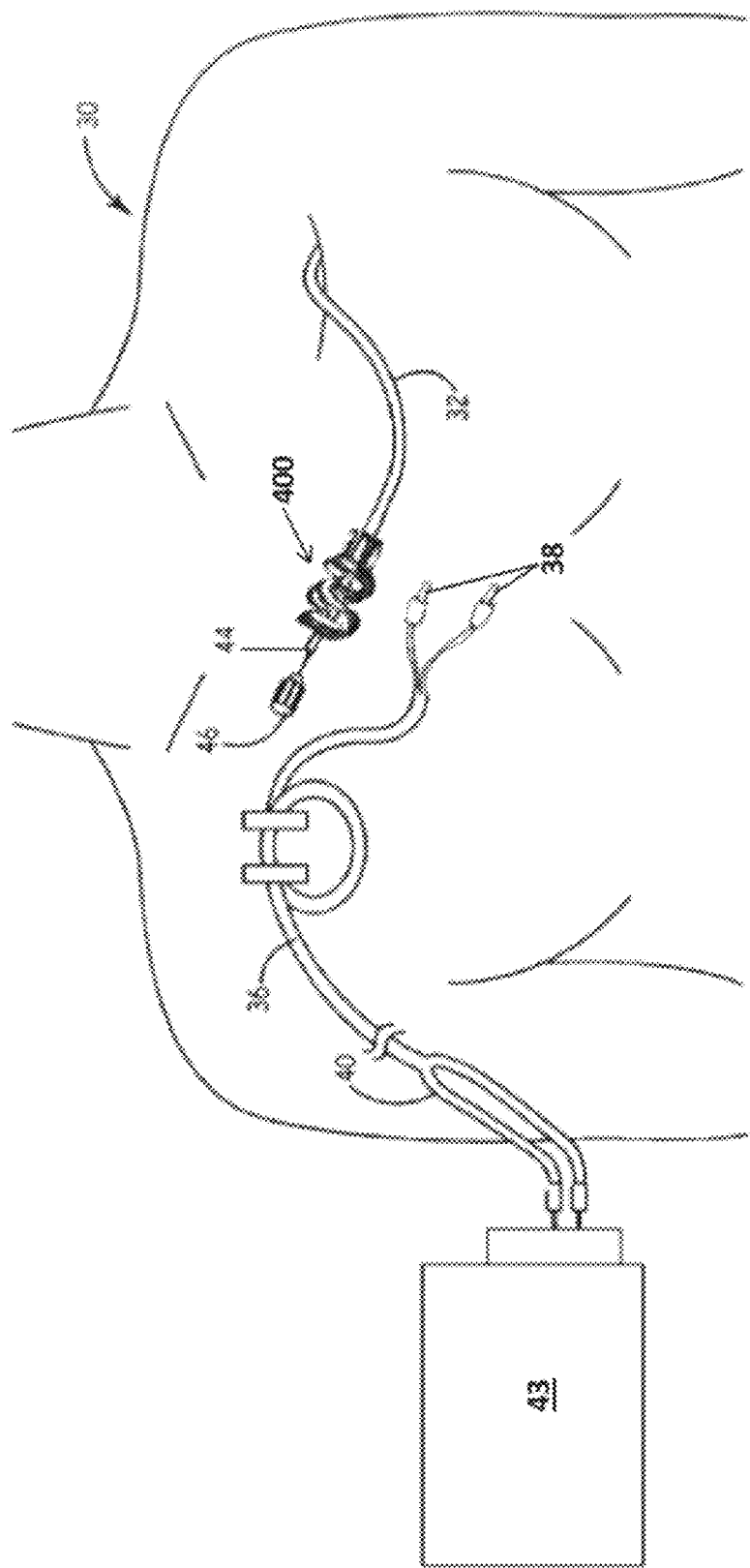
FIG. 1 is a schematic providing context for embodiments of the present invention.

FIG. 1 is a schematic showing a portion of a body 30 of a patient in which a medical electrical lead 32, for example, a cardiac lead, has been implanted, such that a proximal portion thereof extends outside body 30. With reference to FIG. 1, those skilled in the art understand that a distal portion (not shown) of lead 32, to which stimulation and/or sensing electrodes are mounted, has been implanted, either endocardially or epicardially, with the assistance of a stylet 46, inserted within a lumen of lead 32, which may be a standard stylet wire or a hybrid wire having a relatively stiff proximal portion and a relatively flexible, guide wire-like distal portion. As described above, prior to coupling the implanted lead to an implantable pulse generator, an implant evaluation is conducted by means of an external medical device 43 so that, if necessary, the distal portion of lead 32 may be repositioned to place the electrodes thereof in a more effective position for therapy delivery. Examples of medical device 43 include, without limitation, Models 2290 and 8090 Pace Sense Analyzers and Models 5348 and 5388 temporary pacemakers, all provided by Medtronic, Inc. of Minneapolis, Minn. FIG. 1 illustrates an exemplary electrical connection cable 36 for device 43 including a bifurcated connector 40, at one end thereof, which may be plugged into device 43, for electrical connection thereto, and a pair of contact members 38 at another end thereof; each of contact members 38 may be an alligator-type clip, which is shown in greater detail in FIG. 3A. FIG. 1 further illustrates an interface adapter 400, embodiments of which will be described below, assembled onto a connector terminal of lead 32 in order to facilitate temporary electrical connection with device 43, via contact members 38, for the implant evaluation.

FIG. 2 is a perspective view of an exemplary connector terminal 50 of lead 32, for which interface adapter 400, according to some embodiments, is configured. FIG. 2 illustrates connector terminal 50 including a plurality of connector contacts 52, 54, 56 and 44 spaced apart and electrically isolated from one another along a length of terminal 50 by a plurality of insulator members 62, 64 and 66. Each connector contact 52, 54, 56 and 44 may be coupled to a corresponding electrode of lead 32 by an elongate conductor according to a variety of lead construction methods known to those skilled in the art. According to some preferred embodiments of the present invention, interface adapter 400 is configured for compatibility with an embodiment of connector terminal 50 that conforms to the aforementioned IS-4 standard, ISO/FDIS 27186:2009(E), which is hereby incorporated by reference in its entirety. It should be noted that the IS-4 standard dictates shorter connector contact surfaces than prior connector terminal standards, for example, the international standard, ISO 5841-3:2000, for low-profile connectors of implantable pacemakers, which is more commonly known as the IS-1 standard. In addition, the insulator members (i.e. members 62, 64, 66) of connector terminals conforming to the IS-4 standard do not include sealing rings, which were previously typical, but, instead, provide relatively smooth sealing surfaces for sealing rings that are mounted within mating connector bores of implantable pulse generators.

FIG. 3A is a perspective view of alligator-type clip contact member 38, in which opposing contact surfaces 318, formed on opposing jaws 382 thereof, can be seen. Contact surfaces 318 of alligator-type contact clips, which are well known in the art, are characterized by pairs of rows of jagged tooth-like protrusions that make relatively stable and reliable electrical contact, for example, with connector contacts 52, 54, 56, 44, when jaws 382 are clamped down thereon. Thus, with reference to FIG. 2, it may be appreciated that, if contact member 38 is clipped onto connector terminal 50, such that any part of contact surfaces 318 rests against one of insulator members 62, 64, 66, the surface of the insulator member may become indented or scratched so that subsequent sealing with the aforementioned sealing rings of the mating pulse generator connector bore could be compromised. In order to evaluate stimulation efficacy of implanted lead 32, the act of making a stable connection between contact member 38 and lead connector terminal 50, while assuring that no part of contact surfaces 318 rests against one of insulator members 62, 64, 66, could be somewhat tedious or even almost impossible for the implant operator, depending upon a width w of jaws 382, but for interface adapter 400, embodiments of which will now be described.

Figures 4B, 4C, 4D:
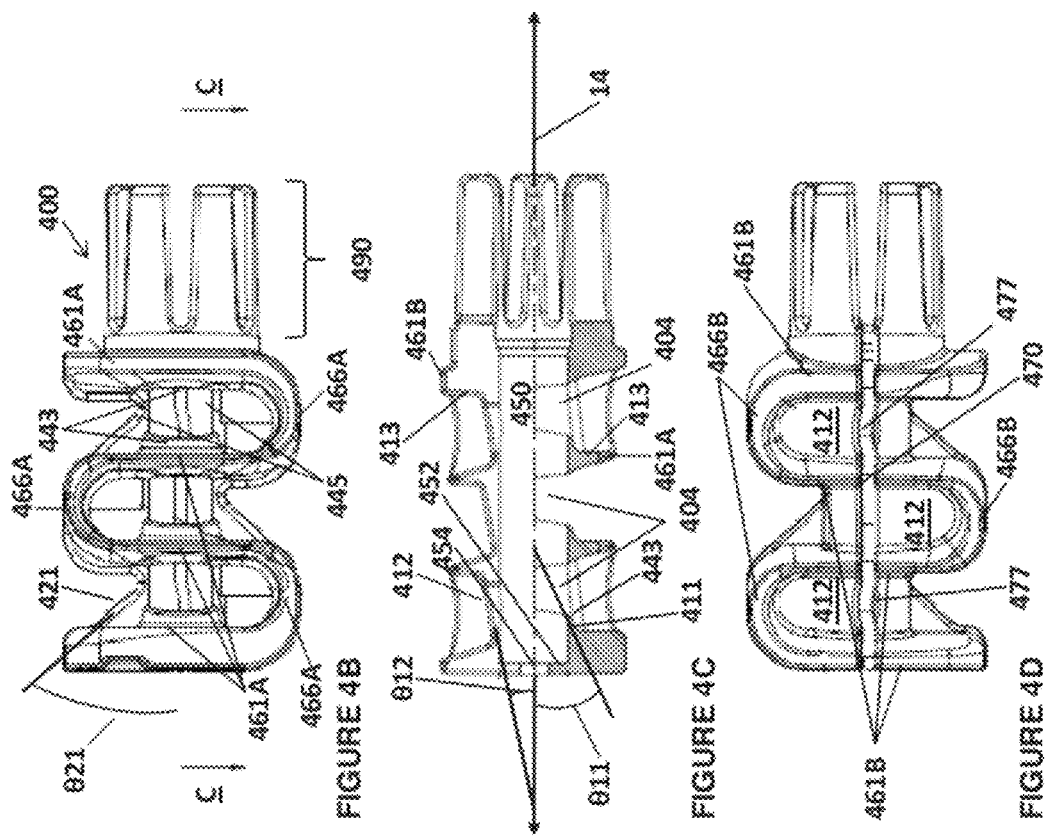
FIGS. 4B-D are a top plan view, a cross-section view and a bottom plan view, respectively, of the interface adapter, according to some embodiments.
Figure 4A:
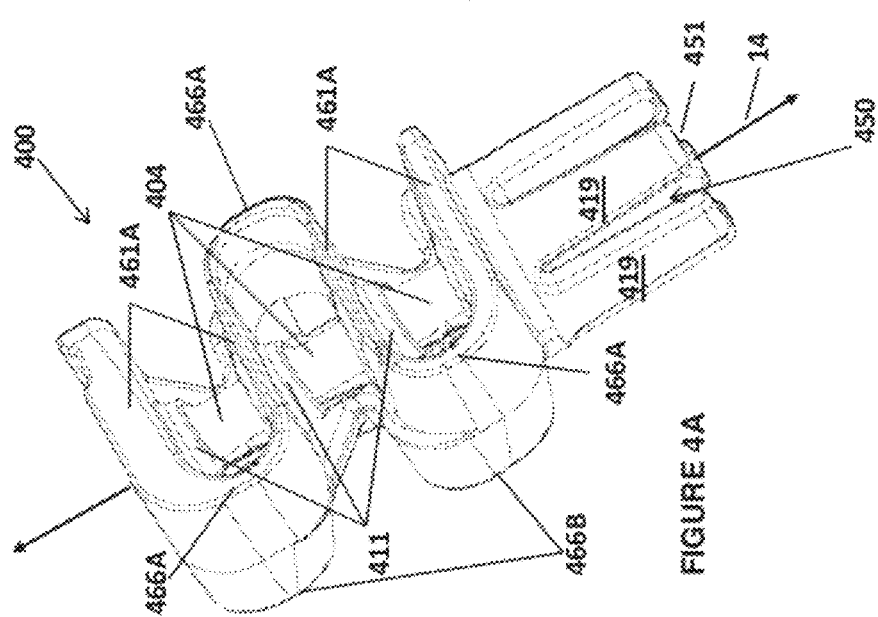
FIG. 4A is a perspective view of an interface adapter, according to some embodiments of the present invention.

FIG. 4A is a perspective view of interface adapter 400, according to some embodiments of the present invention; and FIGS. 4B-D are a top plan view, a cross-section view and a bottom plan view, respectively, of interface adapter 400, according to some embodiments. FIGS. 4A-D illustrates adapter 400 including a receptacle 450, that extends along a longitudinal axis 14 of adapter 400, being surrounded by a sidewall of adapter 400, and contact openings 404, which are formed through the sidewall. The sidewall of adapter 400 is preferably wholly formed, for example, by injection molding, from a relatively hard plastic material such as acetal, polycarbonate, polypropylene and polyethylene, to name a few. According to the illustrated embodiment, and with reference back to FIGS. 1 and 2, receptacle 450 is sized to receive a connector terminal of an implantable medical electrical lead, for example, connector terminal 50 of lead 32, by inserting pin connector contact 44 into a distal opening 451 thereof. Contact openings 404 are sized and positioned along longitudinal axis 14 so as to expose, through the sidewall of adapter 400, connector contacts 52, 54 and 56, when connector terminal 50 is inserted within receptacle 450; and, according to some preferred embodiments, when connector terminal 50 is fully inserted, pin connector contact 44 passes out through a proximal opening 454 (FIG. 4C) of receptacle 450 to protrude proximally from adapter 400, as illustrated in FIGS. 1, 5A-B and 6A-B. Such a protrusion of pin connector contact 44 not only exposes the contact for electrical connection with a contact member, such as member 38, but also allows for the attachment of a torque tool, if lead 32 includes a screw-in helix electrode that is attached, via a conductor coil, to pin connector contact 44 for the activation thereof, according to typical lead construction known in the art. With reference to FIG. 4C, receptacle 450 preferably includes a shoulder 452 in proximity to proximal opening 454 against which a facing portion 57 (FIG. 2) of connector terminal 50 abuts, when connector terminal 50 is fully inserted within receptacle 450, in order to register each of connector contacts 52, 54, 56 with the corresponding opening 404 of adapter 400.

Figure 6A:
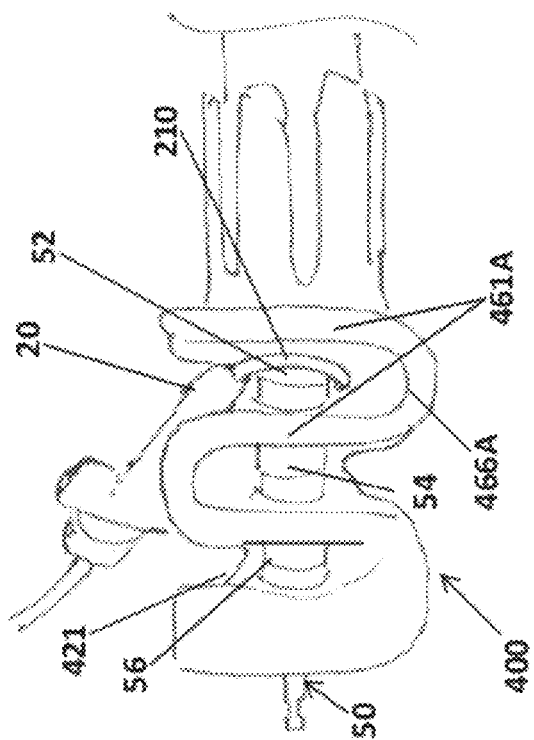
FIGS. 6A-B are top views of the two types of contact members, shown in FIGS. 3A-B, held in electrical contact with a connector terminal on which the interface adapter is assembled, according to some embodiments.

With further reference to FIGS. 4A-D, interface adapter 400 further includes a ridge that includes laterally extending portions 461A, 461B, which are spaced apart from one another along longitudinal axis 14, and connecting portions 466A, 466B, which extend between and connect respective adjacent laterally extending portions 461A, 461B, for example, to augment a longitudinal rigidity of adapter 400. Portions 461A, 466A are shown protruding outward from a side of adapter 400 that corresponds to openings 404, and portions 461B, 466B are shown protruding outward from an opposite side. According to the illustrated embodiment, the ridge creates an alignment guide for positioning an alligator-type clip contact member, for example, contact member 38 (FIG. 3A), over any of contact openings 404 to make electrical contact with the corresponding exposed connector contact member. With reference to FIGS. 4C and 5A, adjacent laterally extending portions 461A, 461B of the ridge, which are spaced apart from one another along longitudinal axis 14 and are located on opposite sides of axis 14, have facing surfaces 413 that extend approximately perpendicular to axis 14 to create a gap g, between which opposing jaws 382 of contact member 38 (FIG. 3A) fit, as will be described in greater detail, below. The ridge further segregates and isolates adjacent connected contact members from one another, for example, as illustrated in FIG. 6A.

FIGS. 4C-D, in conjunction with FIG. 5A further illustrate a canted external edge 412 adjacent to each contact opening 404, wherein each edge 412 has a surface area that extends on an opposite side of longitudinal axis 14 from the corresponding opening 404 and at an angle θ12 with respect to longitudinal axis 14. According to the illustrated embodiment, and with reference back to FIGS. 3A-B, when connector terminal 50 is inserted within receptacle 450 and opposing jaws 382 of contact member 38 are clamped around opening 404, for example, as illustrated in FIG. 6A, one pair of rows of tooth-like protrusions 318, of one of jaws 382 of contact member 38 can rest against canted external edge 412, while one of the rows of the pair of tooth-like protrusions 318 of the corresponding opposing jaw 382 can make electrical contact, through the adjacent contact opening 404, with the exposed connector contact of connector terminal 50. In other words, each canted external edge 412 provides an interface that holds an individual contact member 38 in a 'tilted' orientation, at substantially angle θ12, in order to bias one of contact surfaces 318 thereof through the corresponding contact opening 404 and into electrical contact with the corresponding exposed connector contact.

According to some embodiments, angle θ12 may be greater than approximately 5 degrees and less than 90 degrees, preferably approximately 30 degrees. However, with further reference to FIG. 5A, in conjunction with FIG. 3A, according to some alternate embodiments, if gap g, which is defined between facing surfaces 413 of the above-described ridge, is less than width w of jaws 382 of contact member 38, surfaces 413 can hold jaws 382 in the tilted orientation, such that angle θ12 is not critical and may be closer to, or approximately equal to, 0 degrees. FIG. 5A illustrates, with dots, exemplary locations of contact surfaces 318 of two different widths w of alligator-type clip contact member 38, when clamped around opening 404; and dashed lines in FIG. 5A illustrate a representative profile of the opposing jaws 382 of each width of contact member 38. With reference to the left-hand side of FIG. 5A, a relatively wide contact member is shown interfacing with surfaces 413, only fitting therebetween by virtue of the tilted orientation that biases one of the contact surfaces thereof into electrical contact with connector contact 56. Depending upon the difference between gap g and width w (FIG. 3A), the contact surfaces 318 of the jaw 382 that is adjacent external edge 412 may or may not rest against the surface area thereof. With reference to the right-hand side of FIG. 5A, a relatively narrow contact member is shown fitting loosely between facing surfaces 413, such that the illustrated angle of external edge 412, for example, angle θ12 at greater than approximately 5 degrees, functions to hold contact member 38 in the tilted orientation so that one of the contact surfaces is in electrical contact with connector contact 52. Thus, it may be appreciated that embodiments of adapter 400 may be configured to accommodate a range of widths w of alligator-type clip contact members 38, for example, as illustrated, or may be configured without concern for narrower contact members 38, relying solely on surfaces 413 to hold those contact members 38, whose width w is greater than gap g, in the tilted orientation. An exemplary range of widths w for contact member 38, that can be accommodated by certain embodiments of adapter 400, is from approximately 0.05 inch to approximately 0.15 inch.

With further reference to FIGS. 4A-C and 5A, according to some embodiments, another external edge 411 is located on an opposite side of longitudinal axis 14 from each corresponding edge 412, such that a surface area of each extends directly from a laterally extending side 443 of the corresponding contact opening 404. External edge 411 is preferably canted so that the surface area thereof may further support and/or force jaws 382 of contact member 38 (FIG. 3A) into a position where one of the contact surfaces 318 thereof can make contact through the corresponding opening 404. The surface area of external edge 411, when canted, as illustrated, extends at an angle θ11, which may be approximately equal to angle θ12, or, preferably, steeper (>θ12). With reference to the left-hand side of FIG. 5A, the dashed-line profile of the relatively wide contact member 38 is shown with one of the contact surfaces of one of the jaws thereof located (dot) in proximity to external edge 411 such that, depending on the width w of the contact member 38 relative to gap g, the contact surface may be supported on edge 411 while the other contact surface of the jaw makes electrical contact with connector contact 56. For this relatively wide contact member 38, angle θ11 is not so critical. With reference to the right-hand side of FIG. 5A, the dashed-line profile of the relatively narrow contact member 38 is shown with one of the contact surfaces thereof located over the corresponding contact opening 404 but not contacting/interfacing either with external edge 411 or with the inserted connector terminal 50. For this relatively narrow contact member 38, a relatively steep angle, θ11, of the surface area of external edge 411, causes the corresponding jaw of the narrow contact member to slide toward opening 404, when initially clamped over opening 404, in order to force one of the contact surfaces thereof into contact with connector contact 52, as illustrated.

Figure 6B:
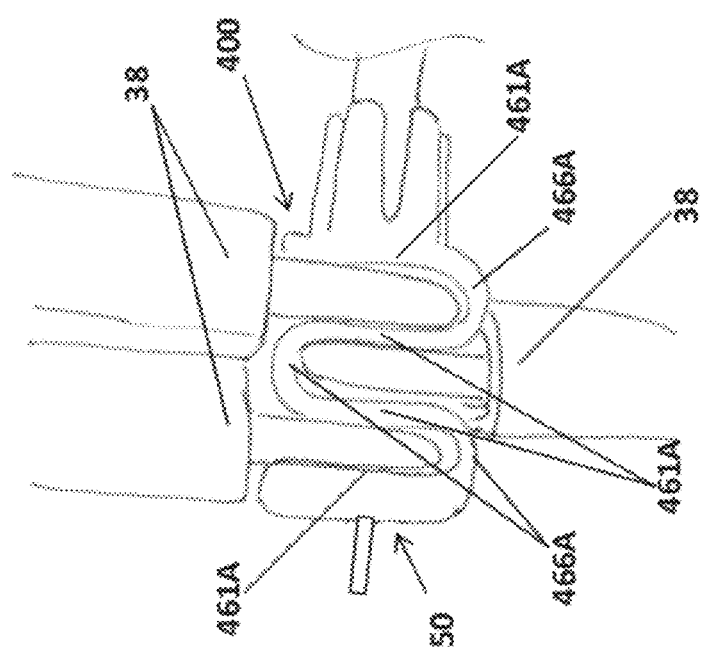

Turning back to FIG. 3B, a j-type clip contact member 20, which is well known to those skilled in the art, is shown having a contact surface designated by reference numeral 210; and, according to some embodiments of the present invention, interface adapter 400 is configured to also provide a suitable interface for contact member 20. With reference to FIGS. 4B, 5B and 6B, the sidewall of interface adapter 400 further includes another set of external edges 421, wherein each edge 421 is located adjacent the corresponding contact opening 404, between adjacent laterally extending portions 461A, 461B, of the above-described ridge, and extends from a longitudinally extending side 445 of the corresponding opening 404. According to the illustrated embodiment, each external edge 421 is canted and extends from the corresponding side 445 at an angle θ21 with respect to longitudinal axis 14 in order guide and bias, substantially at angle θ21, contact surface 210 of contact member 20 through the corresponding opening 404 and into electrical contact with the corresponding exposed connector contact, for example, as illustrated in FIG. 6B. Angle θ21 may be greater than approximately 5 degrees and less than 90 degrees, preferably approximately 45 degrees. However, with reference to the dotted line in FIG. 5B, according to some alternate embodiments, external edge 412 can extend perpendicular to longitudinal axis 14. In either case, interface adaptor 400, as illustrated, may accommodate both alligator-type clip contact members 38 and j-type clip contact members 20, depending upon which type is available to the implant operator.

With further reference to FIGS. 4A-B and D, each connecting portion 466A, 466B of the above-described ridge is shown laterally offset from the corresponding contact opening 404 in alternating directions, such that adjacent connecting portions 466A, 466B are located on opposite sides of longitudinal axis 14 and the ridge extends in a serpentine fashion along a length of adapter 400. An advantage of the illustrated embodiment, in which the ridge extends in the serpentine fashion, may be appreciated with reference to FIG. 6A. FIG. 6A illustrates adaptor 400 accommodating a plurality of alligator-type clip contact members 38, wherein each contact member 38 is connected to the corresponding connector contact 52, 54, 56 (FIG. 5B) of connector terminal 50, simultaneously. When connector terminal 50 conforms to the aforementioned IS-4 standard, a spacing between adjacent connector contacts is such that certain sizes of alligator-type clip contact members may not fit in side-by-side simultaneous contact with the connector contacts, thus the serpentine formation of the ridge guides adjacent contact members 38 from opposite sides, as shown in FIG. 6A. However, according to alternate embodiments, each connecting portion 466A, 466B can extend on a same side of axis 14, so that contact members 38, 20 can all be positioned on an opposite side, side-by-side, for contact with adjacent connector contacts of the connector terminal. Such alternate embodiments accommodate smaller sizes of contact members, that will fit side-by-side, and/or connector terminals that have a larger spacing between connector contacts, than that dictated by the IS-4 standard. Furthermore, according to additional alternate embodiments, laterally extending portions 461A, 461B of the ridge need not be connected together by connecting portions 466A, 466B, so that contact members 38, 20 can be positioned for contact with the exposed connector contacts from either side.

Figure 7:
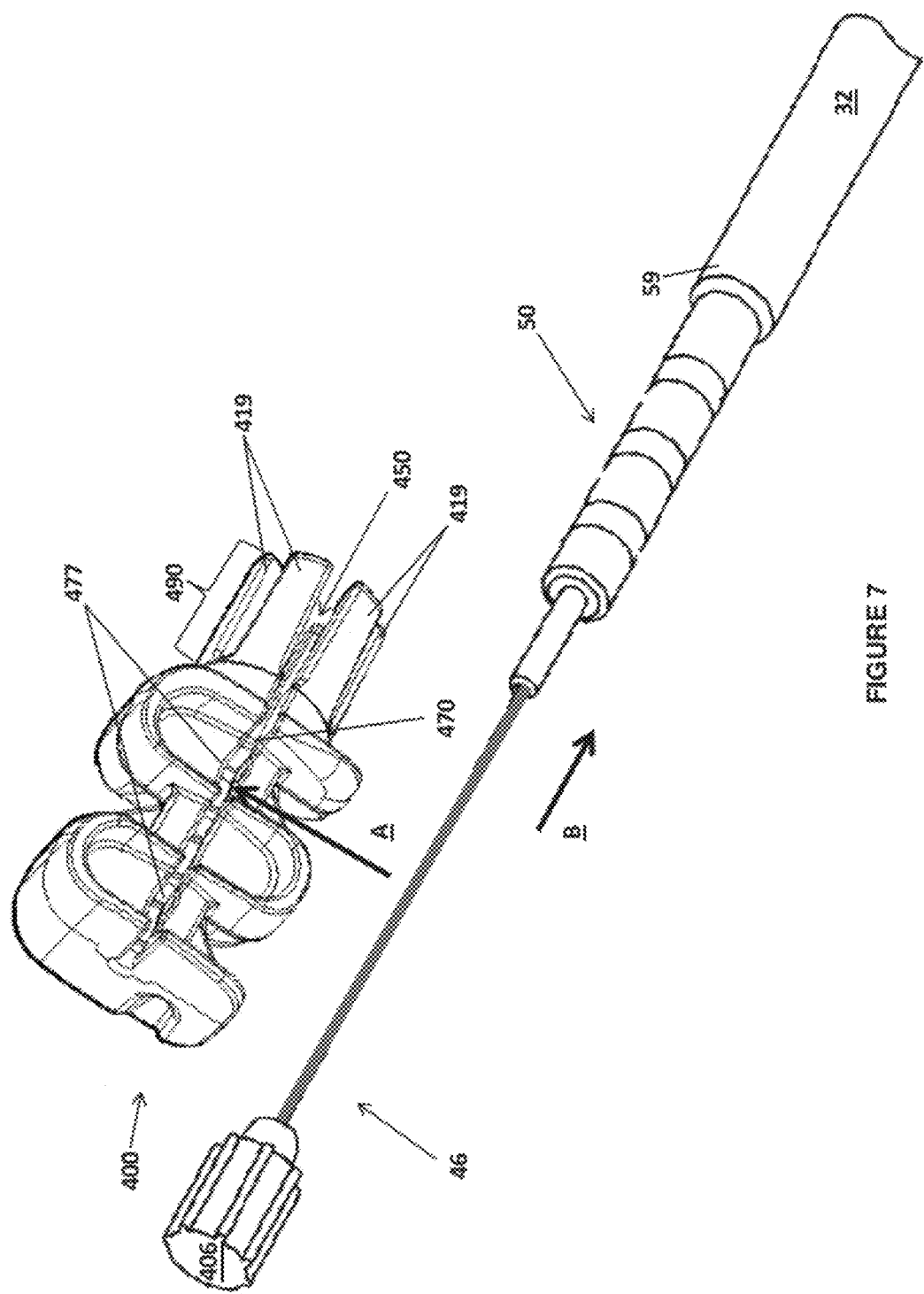
FIG. 7 is a perspective view of the interface adapter positioned for assembly onto the connector terminal of FIG. 2, according to some embodiments.

FIG. 7 is a perspective view of interface adapter 400 positioned for assembly onto connector terminal 50 of lead 32, according to some embodiments, wherein stylet 46 extends within the lumen of lead 32, having assisted in the implantation of lead 32, according to methods known in the art and as depicted in FIG. 1. FIG. 7 illustrates adapter 400 including a slot 470 (also shown in FIG. 4D) formed through the sidewall thereof and extending longitudinally along a length of adapter 400 to provide access to receptacle 450 for stylet insertion per arrow A, since stylet 46 includes a knob 406 that, in many instances, is too large to pass through an entirety of receptacle. The relatively large size of knob 406 facilitates maneuvering of stylet 46 during lead implant. Once stylet 46 is inserted within receptacle 450, adapter 400 may be moved, per arrow B, to subsequently insert connector terminal 50 into receptacle 450, for example as illustrated in FIGS. 1, 5A-B and 6A-B. Although stylet 46 may be removed from lead 32 prior to inserting connector terminal 50 into adapter 400, thereby making slot 470 unnecessary in some alternate embodiments, it is preferable to retain stylet 46 within lead 32 during the implant evaluation, for example, so that, if it is determined that lead 32 needs to be repositioned, to place electrodes in a more effective position, the added step of reinserting stylet 46 is not necessary. According to the illustrated embodiment, one or more optional bends 477 are formed slot 470 to help retain adapter 400 on stylet 46, prior to inserting connector 50 into receptacle 450, by preventing stylet 46 from easily slipping back out from receptacle 450, through slot 470.

FIG. 7 further illustrates lead connector terminal 50 including a distal gripping portion 59, which, when lead connector terminal 50 is fully inserted into receptacle 450 of adapter 400, is contained within a gripping segment 490 of adapter 400, for example, as illustrated in FIGS. 1, 5A-B and 6A-B. According to the illustrated embodiment, the sidewall of adapter 400 includes a plurality of cantilever members 419 that extend distally along longitudinal axis 14 (FIG. 4A) and are spaced apart from one another about a perimeter of receptacle 450 to form gripping segment 490. The nature of cantilever members 419 allows gripping segment 490 to expand and contract for a snug fit around distal gripping portions 59 of various diameters, for example, to hold adapter 400 in place, with each contact opening 404 registered to the corresponding connector contact. Cantilever members 419 can further allow the operator to compress gripping segment 490 around distal gripping portion 59 in order to transfer torque to a body of lead 32, if necessary, in order to reposition lead 32 while retaining adapter 400 in position for further implant evaluation.

In the foregoing detailed description, the invention has been described with reference to specific embodiments. However, it may be appreciated that various modifications and changes can be made without departing from the scope of the invention as set forth in the appended claims. For example, although illustrated embodiments of interface adapter 400 include three contact openings 404, alternate embodiments of the invention may include a single contact opening or other suitable numbers of contact openings, according to that desired for implant evaluation in conjunction with lead connector terminals that are either similar to connector terminal 50 or that have a fewer or greater number of connector contacts. Furthermore, although the illustrated embodiments have been described for use in conjunction with a lead connector terminal that conforms to the IS-4 standard, alternate embodiments of an interface adapter that are configured for alternate forms of medical electrical lead connectors, yet employ any of the inventive aspects described and claimed herein are not outside the scope of the present invention.

We claim:

1. An interface adapter for an implantable medical electrical lead, the interface adapter facilitating temporary electrical connection between an external medical device and a connector terminal of the medical electrical lead, the interface adapter including a longitudinal axis, a receptacle extending along the longitudinal axis and being sized to receive insertion of the lead connector terminal therein, a sidewall surrounding the receptacle, and a contact opening being formed through the sidewall to the receptacle, the contact opening being positioned along the longitudinal axis of the interface adapter so as to expose, through the sidewall, a connector contact of the lead connector terminal, when the lead connector terminal is inserted within the receptacle, for electrical connection with a contact surface of a contact member of an electrical connection cable for the external medical device; and wherein the sidewall of the interface adapter comprises:

a canted external edge adjacent to the contact opening; and wherein the canted external edge has a surface area that extends at an angle with respect to the longitudinal axis of the interface adapter, to provide an interface that holds the contact member in a tilted orientation, at substantially the same angle, in order to bias the contact surface of the contact member through the contact opening and into electrical contact with the exposed connector contact of the lead connector terminal, when the lead connector terminal is inserted within the receptacle of the interface adapter, the angle being greater than approximately 5 degrees and less than 90 degrees.

2. The interface adapter of claim 1, wherein the surface area of the canted external edge extends on an opposite side of the longitudinal axis from the contact opening.

3. The interface adapter of claim 2, wherein:
the contact opening has a perimeter defined, at least in part, by a longitudinally extending side and a laterally extending side, the laterally extending side being approximately orthogonal to the longitudinal axis of the interface adapter; the canted external edge of the sidewall comprises a first canted external edge of a pair of first and second canted external edges of the sidewall;
a surface area of the second canted external edge extends from the laterally extending side of the contact opening, at an angle that is approximately the same or greater than that of the first canted external edge, and in one of a proximal direction and a distal direction along the longitudinal axis of the interface adapter; and
the surface area of the first canted external edge extends in the other of the proximal and distal directions along the longitudinal axis.

4. The interface adapter of claim 1, wherein:
the contact opening has a perimeter defined, at least in part, by a longitudinally extending side and a laterally extending side, the laterally extending side being approximately orthogonal to the longitudinal axis of the interface adapter; and
the surface area of the canted external edge extends from the laterally extending side of the contact opening.

5. The interface adapter of claim 1, wherein:
the contact opening has a perimeter defined by a pair of opposing longitudinally extending sides and a pair of opposing laterally extending sides, between which the opposing longitudinally extending sides extend; and
the canted external edge extends from one of the opposing longitudinally extending sides of the contact opening at a point in between the pair of opposing laterally extending sides.

6. The interface adapter of claim 1, wherein:
the sidewall further comprises another external edge;
the contact opening has a perimeter defined by a pair of opposing longitudinally extending sides and a pair of opposing laterally extending sides, between which the opposing longitudinally extending sides extend; and
the other external edge extends from one of the opposing longitudinally extending sides of the contact opening at a point in between the pair of opposing laterally extending sides.

7. The interface adapter of claim 1, wherein:
the contact opening is one of a plurality of contact openings spaced apart from one another along the longitudinal axis of the interface adapter so as to expose, through the sidewall, a corresponding plurality of connector contacts of the lead connector terminal, when the lead connector terminal is inserted within the receptacle, for electrical connection of each connector contact with the contact surface of a corresponding contact member of the electrical connection cable;

each contact opening of the plurality of contact openings has a perimeter defined, at least in part, by a longitudinally extending side and a laterally extending side, the laterally extending side being approximately orthogonal to the longitudinal axis of the interface adapter;
the canted external edge of the sidewall is one of a plurality of canted external edges, each of the plurality of canted external edges being a first canted external edge of a corresponding pair of first and second canted external edges of a plurality of pairs of canted external edges;
the surface area of each first canted external edge extends on an opposite side of the longitudinal axis from the corresponding contact opening, at the angle and in one of a proximal direction and a distal direction along the longitudinal axis of the interface adapter; and
each second canted external edge extends from the laterally extending side of the corresponding contact opening, and has a surface area that extends in the other of the proximal and distal directions along the longitudinal axis.

8. The interface adapter of claim 7, wherein:
the sidewall further comprises a ridge extending along the longitudinal axis of the interface adapter in a serpentine fashion, the ridge protruding outward from the plurality of contact openings; and
the ridge includes laterally extending portions and connecting portions, the laterally extending portions spaced apart from one another along the longitudinal axis of the interface adapter, on opposing sides of each of the plurality of contact openings, and each of the connecting portions extending between adjacent laterally extending portions of the ridge and being laterally offset, in alternating directions, from the corresponding contact opening, such that adjacent connecting portions are located on opposite sides of the longitudinal axis of the interface adapter.

9. The interface adapter of claim 8, wherein the ridge further protrudes outward from the first canted external edges.

10. The interface adapter of claim 7, further comprising a slot formed through the sidewall, opposite the plurality of contact openings, the slot providing access to the receptacle and extending longitudinally along a length of the sidewall.

11. The interface adapter of claim 10, wherein the slot includes one or more bends formed therein.

12. The interface adapter of claim 7, wherein the receptacle includes a shoulder against which a portion of the lead connector terminal abuts, when the connector terminal is fully inserted within the receptacle, in order to register each of the plurality of connector contacts of the connector terminal with the corresponding contact opening.

13. The interface adapter of claim 12, wherein the receptacle further includes an opening extending proximally from the shoulder, the opening being sized to allow a pin connector contact of the lead connector terminal to extend proximally from the interface adapter, outside the receptacle, when the portion of the connector terminal abuts the shoulder of the receptacle.

14. The interface adapter of claim 7, wherein the sidewall further comprises a plurality of cantilever members spaced apart from one another about a perimeter of the receptacle to form a gripping segment, the cantilever members extending distally, along the longitudinal axis, from the plurality of contact openings.

15. The interface adapter of claim 1, further comprising a slot formed through the sidewall, opposite the contact opening, the slot providing access to the receptacle and extending longitudinally along a length of the sidewall.

16. The interface adapter of claim 15, wherein the slot includes one or more bends formed therein.

17. The interface adapter of claim 1, wherein the receptacle includes a proximal opening, the proximal opening being sized to allow a pin connector contact of the lead connector terminal to extend proximally from the interface adapter, outside the receptacle, when the connector terminal is inserted within the receptacle.

18. The interface adapter of claim 1, wherein the sidewall further comprises a plurality of cantilever members spaced apart from one another about a perimeter of the receptacle to form a gripping segment, the cantilever members extending distally, along the longitudinal axis, from the contact opening.

19. An interface adapter for an implantable medical electrical lead, the interface adapter facilitating temporary electrical connection between an external medical device and a connector terminal of the medical electrical lead, the interface adapter including a longitudinal axis, a receptacle extending along the longitudinal axis and being sized to receive insertion of the lead connector terminal therein, a sidewall surrounding the receptacle, and a plurality of contact openings being formed through the sidewall to the receptacle, each contact opening being positioned along the longitudinal axis of the interface adapter so as to expose, through the sidewall, a corresponding connector contact of a plurality of connector contacts of the lead connector terminal, when the lead connector terminal is inserted within the receptacle, for electrical connection with a contact surface of a corresponding contact member of an electrical connection cable for the external medical device; and wherein the sidewall of the interface adapter comprises:
- a plurality of canted external edges, each canted external edge adjacent to a corresponding one of the contact openings; and
- wherein each canted external edge has a surface area that extends at an angle with respect to the longitudinal axis of the interface adapter to provide an interface that holds the corresponding contact member in a tilted orientation, at substantially the same angle, in order to bias the contact surface of the corresponding contact member through the corresponding contact opening and into electrical contact with the corresponding exposed connector contact of the lead connector terminal, when the lead connector terminal is inserted within the receptacle of the interface adapter, the angle being greater than approximately 5 degrees and less than 90 degrees.

20. The interface adapter of claim 19, wherein:
- the sidewall further comprises a ridge extending along the longitudinal axis of the interface adapter in a serpentine fashion, the ridge protruding outward from the plurality of contact openings; and
- the ridge includes laterally extending portions and connecting portions, the laterally extending portions spaced apart from one another along the longitudinal axis of the interface adapter, on opposing sides of each of the plurality of contact openings, and each of the connecting portions extending between adjacent laterally extending portions of the ridge and being laterally offset, in alternating directions, from the corresponding contact opening, such that adjacent connecting portions are located on opposite sides of the longitudinal axis of the interface adapter.

21. The interface adapter of claim 19, further comprising a slot formed through the sidewall, opposite the plurality of contact openings, the slot providing access to the receptacle and extending longitudinally along a length of the sidewall.

22. The interface adapter of claim 21, wherein the slot includes one or more bends formed therein.

23. The interface adapter of claim 19, wherein the receptacle includes a shoulder against which a portion of the lead connector terminal abuts, when the connector terminal is fully inserted within the receptacle, in order to register each of the plurality of connector contacts of the connector terminal with the corresponding contact opening.

24. The interface adapter of claim 23, wherein the receptacle further includes an opening extending proximally from the shoulder, the opening being sized to allow a pin connector contact of the lead connector terminal to extend proximally from the interface adapter, outside the receptacle, when the portion of the connector terminal abuts the shoulder of the receptacle.

25. The interface adapter of claim 19, wherein the receptacle includes a proximal opening, the proximal opening being sized to allow a pin connector contact of the lead connector terminal to extend proximally from the interface adapter, outside the receptacle, when the connector terminal is inserted within the receptacle.

26. The interface adapter of claim 19, wherein the sidewall further comprises a plurality of cantilever members spaced apart from one another about a perimeter of the receptacle to form a gripping segment, the cantilever members extending distally, along the longitudinal axis, from the plurality of contact openings.

27. An interface adapter for an implantable medical electrical lead, the interface adapter facilitating temporary electrical connection between an external medical device and a connector terminal of the medical electrical lead, the interface adapter including a longitudinal axis, a receptacle extending along the longitudinal axis and being sized to receive insertion of the lead connector terminal therein, a sidewall surrounding the receptacle, and a contact opening being formed through the sidewall to the receptacle, the contact opening having a perimeter defined by a pair of opposing longitudinally extending sides and a pair of opposing laterally extending sides, between which the opposing longitudinally extending sides extend, and the contact opening being positioned along the longitudinal axis of the interface adapter so as to expose, through the sidewall, a connector contact of the lead connector terminal, when the lead connector terminal is inserted within the receptacle, for electrical connection with a contact surface of a contact member of an electrical connection cable for the external medical device, the contact member being an alligator-type clip having opposing jaws on which the contact surface is formed; and wherein the sidewall of the interface adapter comprises:
- a ridge protruding outward from the contact opening, the ridge including a first laterally extending portion and a second laterally extending portion, the first laterally extending portion located alongside one of the pair of opposing laterally extending sides of the contact opening and the second laterally extending portion located on an opposite side of the longitudinal axis from the contact opening and the first laterally extending portion of the ridge and being spaced apart from the first laterally extending portion along the longitudinal axis; and the first and second laterally extending portions of the ridge include facing surfaces that extend approximately perpendicular to the longitudinal axis, on opposite sides of the axis, the facing surfaces creating a gap between which opposing jaws of the contact member, of a given width, fit in a tilted orientation, the tilted orientation biasing the contact surface of the fitted jaws through the contact opening and into electrical contact with the corresponding exposed connector contact of the lead connector terminal, when the connector terminal is inserted within the receptacle of the interface adapter.

28. The interface adapter of claim 27, wherein the ridge further includes a connecting portion extending between and connecting the first and second laterally extending portions, the connecting portion being offset from the contact opening.

29. The interface adapter of claim 27, further comprising a slot formed through the sidewall, opposite the contact opening, the slot providing access to the receptacle and extending longitudinally along a length of the sidewall.

30. The interface adapter of claim 29, wherein the slot includes one or more bends formed therein.

31. The interface adapter of claim 27, wherein the receptacle includes a proximal opening, the proximal opening being sized to allow a pin connector contact of the lead connector terminal to extend proximally from the interface adapter, outside the receptacle, when the connector terminal is inserted within the receptacle.

32. The interface adapter of claim 27, wherein the sidewall further comprises a plurality of cantilever members spaced apart from one another about a perimeter of the receptacle to form a gripping segment, the cantilever members extending distally, along the longitudinal axis, from the contact opening.

33. The interface adapter of claim 27, wherein the sidewall further comprises a canted external edge adjacent to the contact opening, the canted external edge extending at an angle with respect to the longitudinal axis of the interface adapter, the angle being greater than approximately 5 degrees and less than 90 degrees.

\* \* \* \* \*